(12) United States Patent
Baumgardner et al.

(10) Patent No.: US 7,247,470 B2
(45) Date of Patent: Jul. 24, 2007

(54) METHOD AND APPARATUS FOR MEASURING NITRIC OXIDE PRODUCTION AND OXYGEN CONSUMPTION IN CULTURES OF ADHERENT CELLS

(75) Inventors: James E. Baumgardner, Folsom, PA (US); Cynthia M. Otto, Folsom, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 10/996,395

(22) Filed: Nov. 26, 2004

(65) Prior Publication Data

US 2005/0112549 A1  May 26, 2005

Related U.S. Application Data

(63) Continuation of application No. PCT/US03/17373, filed on Jun. 2, 2003.

(60) Provisional application No. 60/384,136, filed on May 31, 2002.

(51) Int. Cl.
*C12M 1/34* (2006.01)
(52) U.S. Cl. ............... 435/287.5; 435/286.5; 435/293.1; 435/807; 422/79; 422/88
(58) Field of Classification Search ............ 435/287.5, 435/293.1, 807
See application file for complete search history.

(56) References Cited

U.S. PATENT DOCUMENTS

| | | | | |
|---|---|---|---|---|
| 3,954,411 | A | * | 5/1976 | Snyder ..................... 436/53 |
| 4,424,276 | A | * | 1/1984 | Clark et al. ............. 205/777.5 |
| 4,439,679 | A | | 3/1984 | McIlroy et al. |
| 4,629,686 | A | * | 12/1986 | Gruenberg ............... 435/286.5 |
| 5,234,835 | A | * | 8/1993 | Nestor et al. .................. 436/11 |
| 5,434,085 | A | | 7/1995 | Capomacchia et al. |
| 6,133,567 | A | | 10/2000 | Baumgardner |
| 6,269,679 | B1 | | 8/2001 | McCarthy et al. |
| 6,280,604 | B1 | | 8/2001 | Piantadosi et al. |

FOREIGN PATENT DOCUMENTS

WO   WO 9921002 A1 *  4/1999

OTHER PUBLICATIONS

Baumgardner, James E. et al.: "In vitro intermittent hyposia: Challenges for creating hyposia in cell culture." Respiratory Physiology and Neurobiology, vol. 136, No. 2-3, Apr. 10, 2003.
Hallman, T.M. et al: "Oxygen dependence of nitric oxide synthesis in raw 264.7 cells." FASEB Journal, vol. 13, No. 4, Part 1, Mar. 12, 1999.

* cited by examiner

*Primary Examiner*—William H. Beisner
(74) *Attorney, Agent, or Firm*—Womble Carlyle

(57) ABSTRACT

An apparatus and method for measuring nitric oxide production and oxygen consumption in cultures of adherent cells continuously and without destroying the cells. The method involves flowing growth media through a tube having adherent cells are adhered to the inner surface thereof and then contacting the growth media with an NO or $O_2$ sensor to detect the concentration of NO or $O_2$ in the growth media.

26 Claims, 2 Drawing Sheets

METHOD AND APPARATUS FOR MEASURING NITRIC OXIDE PRODUCTION AND OXYGEN CONSUMPTION IN CULTURES OF ADHERENT CELLS

RELATED APPLICATIONS

This is a Continuation of International Application No. PCT/US03/17373, filed Jun. 2, 2003, which was published as WO 03/102124 A2 on Dec. 11, 2003, and claims priority to U.S. Provisional Application No. 60/384,136, filed May 31, 2002. The contents of the aforementioned applications are incorporated by reference in their entirety.

FIELD OF THE INVENTION

The present invention is directed to the field of laboratory instrumentation and techniques, especially those directed to detecting and measuring nitric oxide produced by cultures of adherent cells and oxygen consumption by cultures of adherent cells.

BACKGROUND OF THE INVENTION

Nitric oxide (NO) is involved in a variety of biological processes including, for example, vascular control, neuronal signaling, control of clotting, and modulation of inflammatory responses. Nitric oxide is synthesized in most cells of the body by the enzyme nitric oxide synthase (NOS). Several forms of nitric oxide synthases are known. In an inflammatory response it is believed that the production of NO is a key factor in determining the magnitude of the inflammatory response. The NO produced by cells involved in inflammatory process is produced by a form of nitric oxide synthases called inducible nitric oxide synthases (iNOS). Macrophage cells are an example of cells that produce iNOS.

By measuring the production of NO by cell cultures exposed to various stimuli it is possible to quantify the cells response to the stimuli and, accordingly, whether the stimuli will induce, for example, an inflammatory response and the magnitude of the response. Current methods for measuring the rate of production of NO by cell cultures require extracting the nitric oxide synthases from the cells and then measuring the activity of the extracted nitric oxide synthases in vitro. Typically, the nitric oxide synthases is extracted, the extracted nitric oxide synthases is contacted with the substrates arginine and excess $O_2$, and the rate of formation of citrulline is used to assess nitric oxide synthases activity in vitro. The extraction process, however, can radically change the activity of the nitric oxide synthases. Thus, the assay may not measure the actual activity of nitric oxide synthases in the cells of the cell culture. Also the extraction process destroys the cells.

R. S. Lewis et al. in "Kinetic Analysis of the Fate of Nitric Oxide Synthesized by Macrophages In Vitro" in *Journal of Biological Chemistry*, 270, 29350-29355 (1995) discloses a process for measuring NO production by macrophage cells by adhering the macrophage cells to microbeads, suspending the beads in media in a sealed container with a stirring mechanism to encourage mixing, and measuring NO concentrations in the headspace gas by directly measuring the partial pressure of NO and the partial pressure of the stable end products of NO oxidation, namely $NO_2$ and $NO_3$. In the disclosed method most of NO made by cells is produced at a significant distance from the NO sensor and is oxidized to $NO_2$ and $NO_3$ as it diffuses through the media. Since the NO is oxidized to $NO_2$ and $NO_3$ before it reaches the NO sensor it is not detected by the NO sensor. Accordingly, it is imperative in the disclosed system that the partial pressures of the oxidation products $NO_2$ and $NO_3$ be measured as well as the partial pressure of NO, in order to assess total NO production. Simultaneously measuring the partial pressures of $NO_2$, $NO_3$, and NO, however, is more complicated and time consuming than directly measuring only the partial pressures of NO.

One prior art method for measuring cellular respiration involves culturing adherent cells on plates at the bottom of culture wells and then covering the cells with a layer of media in the usual way. Cellular respiration is then measured using a sensor placed at some point near the cells. Knowing the gradient for the partial pressure of $O_2$ in the media covering the cells and assuming the media has no convective mixing, the diffusion equation is solved to determine cellular respiration. When the partial pressure of $O_2$ is measured by an electrode, this system has been called the open-air method. A system that functions in a similar way is offered commercially by BD Biosciences. In the system of BD Biosciences the partial pressure of $O_2$ is measured by a fluorescent complex at the bottom of the culture well. This approach results in some convective mixing in the media that leads to substantial errors in determining cellular respiration.

Furthermore, prior approaches to controlling the partial pressure of oxygen in adherent cell cultures have suffered from the problem that convection in the growth media surrounding the cells is difficult to control. As a result, the diffusion of oxygen from the headspace gas, through the growth media, and to the cells is highly variable. Because of the variability of diffusion the partial pressure of oxygen at the cellular level is different from the partial pressure of oxygen in the headspace and it is impossible to determine the partial pressure of oxygen at the cellular level. Furthermore, restricted diffusion in the growth media makes it impossible to rapidly change the partial pressure of oxygen at the cellular level because any rapid changes in the partial pressure of oxygen in the headspace are damped out by diffusion through the growth media.

In another prior art method, the cells are grown under the experimental conditions of interest and are then scraped off of the surface they are growing on and re-suspended in media. The media is then placed in a sealed chamber, air bubbles are removed, and the partial pressure Of $O_2$ in the media is measured. The decay in partial pressure of $O_2$ versus time is directly related to cellular respiration. Thus, in the prior art techniques, (1) the cells must be scraped off and suspended, which frequently activates or inactivates adherent cells; (2) complete removal of gas bubbles is difficult, even a tiny bubble can ruin the results; and (3) cellular respiration cannot be changing during the measurement, otherwise the decay rate will not be constant.

SUMMARY OF THE INVENTION

The present invention is directed to a method for measuring NO production by living cells. The method comprises:

providing a tubular member configured to accommodate passage of a growth media therethrough;

adhering the living cells to an inner surface of the tubular member;

flowing a first growth media having a first concentration of $O_2$ dissolved therein, through the tubular member; and detecting a concentration of NO in the first growth media after the first growth media has flowed through the tubular member.

The invention further relates to a method for measuring $O_2$ consumption by living cells. The method comprises:

providing a tubular member configured to accommodate passage of a fluid therethrough;

adhering the living cells to an inner surface of the tubular member;

providing a first growth media having $O_2$ dissolved therein;

flowing at least a first portion of the first growth media through the tubular member such that the living cells are contacted by the first portion;

measuring a first $O_2$ concentration of the first portion after it has contacted the living cells;

measuring a second $O_2$ concentration of a second portion of the first growth media that has not contacted the living cells; and comparing the first concentration of $O_2$ with the second concentration of $O_2$.

In one embodiment of the methods the tubular member is a capillary tube. The capillary tube can be a silica glass tube having an inside diameter of from about 0.01 mm to about 1 mm, an outside diameter of about 0.3 mm to about 1.5 mm, and a length of from about 2 cm to about 100 cm. The inner surface of the capillary tube can be coated with a polar or non-polar coating. For example, the inner surface of the capillary tube can be coated with a siloxane such as phenylmethylsiloxane or dimethylsiloxane. The coating can have a thickness of from about 2 microns to about 50 microns.

The growth media can flow through the tube at a flow rate of from about 0.2 mL/min to about 0.8 mL/min. In one embodiment the media flows through the tube at a flow rate of from about 0.5 mL/min to about 0.6 mL/min.

The concentration of $O_2$ in the growth media can be obtained by passing the growth media through a silicone tube that is surrounded by Tygon® tubing through which oxygen at a partial pressure of $PO_2$ and a second gas of partial pressure PX is flowing. The second gas can be $CO_2$. The silicone tubing can have an inside diameter of from about 0.012 inches to about 0.065 inches, an outside diameter of about 0.020 inches to about 0.080 inches, and a length of from about 3 inches to about 10 feet. The Tygon® tubing can have an inside diameter that is about 10 to 70 percent larger than the outside diameter of the silicone tubing and is about the same length as the silicone tubing The pressure of $O_2$ and $CO_2$ can range from about 0.1 torr to about 500 torr. In one embodiment the silicone tubing has an inside diameter of about 0.02 inches, an outside diameter of about 0.32 inches, and is about 3 feet long.

The invention is also directed to a nitric oxide (NO) measuring apparatus. The NO measuring apparatus comprises:

a first gas equilibrator having an inlet and an outlet, the first gas equilibrator configured to maintain a first concentration of a first gas within a first fluid, when the first fluid flows through the first gas equilibrator;

a tubular member configured to accommodate passage of a fluid therethrough, the tubular member having an inner surface suitable for having living cells adhered thereto, said tubular member having an inlet and an outlet, wherein the inlet of the tubular member is in fluid communication with the outlet of the first gas equilibrator;

a first NO sensor configured to measure an NO concentration of a first effluent from the first gas equilibrator that has flowed through the tubular member; and a first oxygen ($O_2$) sensor configured to measure $O_2$ concentration of a first effluent from the first gas equilibrator that has not flowed through the tubular member.

The apparatus can further comprise a second gas equilibrator configured to maintain a second concentration of a second gas within a second fluid, when said second fluid flows through the second gas equilibrator; wherein the second gas equilibrator is selectively connectable to the inlet of said tubular member.

The apparatus can further comprise a first pump configured to supply the first fluid to the first gas equilbrator and a second pump configured to supply the second fluid to the second gas equilbrator. The first pump and the second pump may be implemented as a single unit.

The apparatus can further comprise a source of nitric oxide selectively connectable to the first NO sensor. The source of NO can be a NO equilibrator configured to maintain a concentration of NO within a third fluid, when said third fluid flows through the NO equilibrator. The third fluid can be deoxygenated water.

The invention further relates to an oxygen ($O_2$) measuring apparatus. The apparatus comprises:

a first gas equilibrator having a first inlet and a first outlet, the first gas equilibrator configured to maintain a concentration of $O_2$ gas within a first fluid, when said first fluid flows through the first gas equilibrator;

a tubular member configured to accommodate passage of a fluid therethrough, the tubular member having an inner surface suitable for having living cells adhered thereto, said tubular member having an inlet and an outlet, wherein the inlet of the tubular member is in fluid communication with the outlet of the first gas equilibrator; and at least one $O_2$ sensor configured to measure (a) $O_2$ concentration of a first effluent from the first gas equilibrator that has flowed through the tubular member; and (b) $O_2$ concentration of a first effluent from the first gas equilibrator that has not flowed through the tubular member.

The oxygen measuring apparatus can comprise a first oxygen sensor that measures the $O_2$ concentration of the first effluent and a separate, second $O_2$ sensor that measures the $O_2$ concentration of the second effluent. Alternatively, the oxygen measuring apparatus can comprise a single $O_2$ sensor configured to selectively measure the $O_2$ concentration in both the first and second effluents, but at different times.

The oxygen measuring apparatus can further comprise a second gas equilibrator configured to maintain a second concentration of $O_2$ gas within a second fluid, when said second fluid flows through the second gas equilibrator; wherein the second gas equilibrator is selectively connectable to the inlet of said tubular member. The first fluid and the second fluid can be the same.

The apparatus can further comprise a first pump configured to supply said first fluid to said first gas equilbrator and a second pump configured to supply said second fluid to said second gas equilbrator. The first pump and the second pump may be implemented as a single unit.

BRIEF DESCRIPTION OF THE DRAWINGS

The present invention is now described with reference to the following drawings in which.

DETAILED DESCRIPTION OF THE INVENTION

Figure 1:
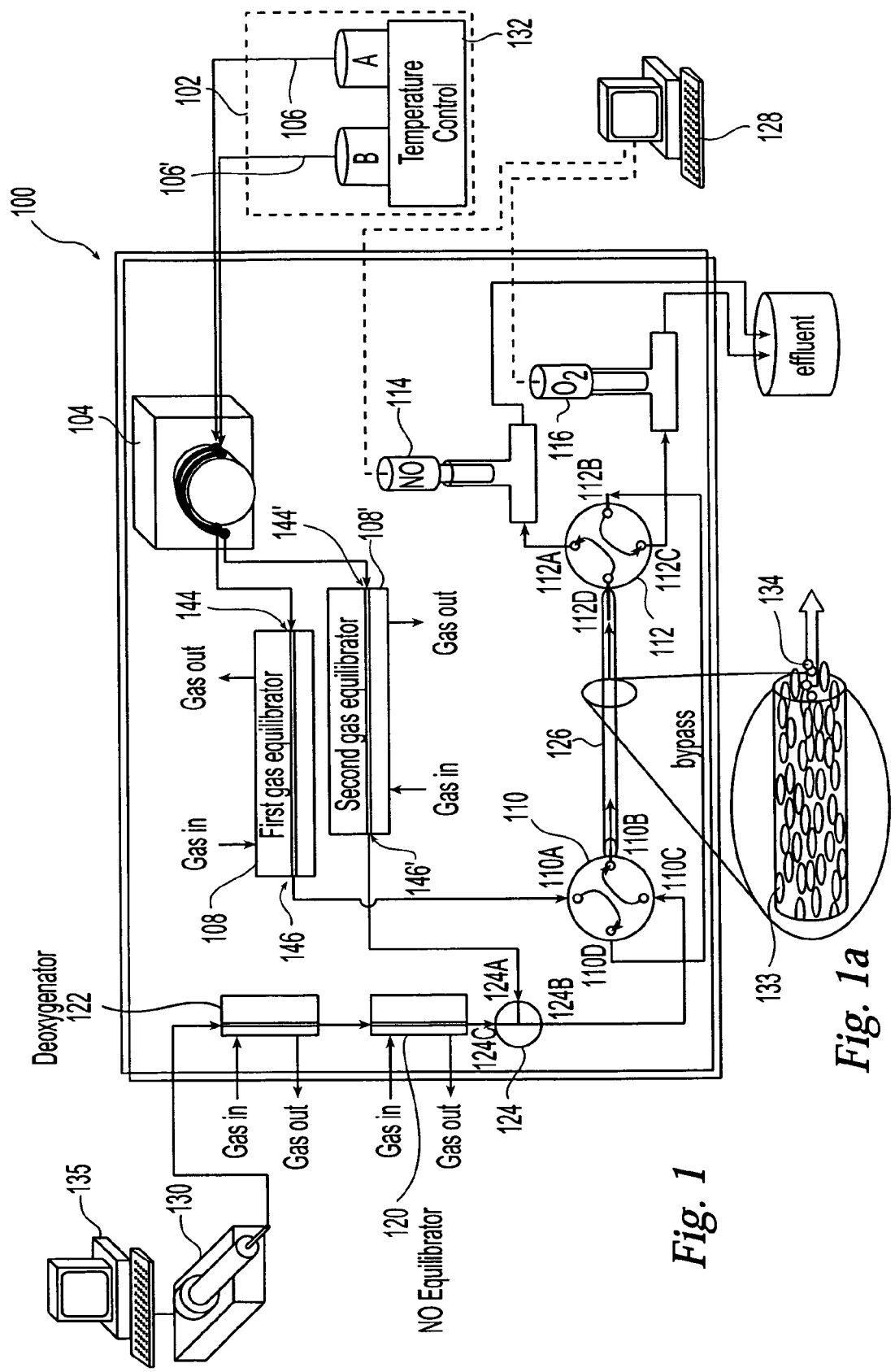
FIG. 1 is a schematic of the apparatus of the invention.

The present invention is directed to an apparatus and a method for measuring the rate of production of NO by adherent cells. As used herein, the term "adherent cells," as used herein means cells that will grow on a surface. Example of adherent cells include, but are not limited to, macrophage cells; endothelial cells; fibroblasts; and parenchymal cells, such as PC-12 cells and hepatoma cell lines. The apparatus and methods of the invention can be used to measure NO production and $O_2$ consumption in adherent cells isolated from animals, preferably humans, that can be grown in a culture. Examples of such adherent cells that can be isolated from animals and grown in culture include, but are not limited to, alveolar macrophages from broncho-alveolar lavage (BAL) fluid in pulmonary disease, especially acute respiratory distress syndrome (ARDS); monocytes in blood samples; peritoneal macrophages from peritoneal lavage; and cells from tissue biopsies. The present invention also contemplates measuring NO production or $O_2$ consumption of living cells that normally are not considered to be adherent cells, but, by some means or other, have been made to adhere to a surface. All of these will henceforth simply be referred to as "cells".

The present invention allows the concentration of NO production in living cells to be measured continuously, directly (i.e., without having to measure $NO_2$ and $NO_3$ concentrations), quantitatively, and without destruction of the cells. According to the method of the invention, the cells are adhered to the inner wall of a tube through which growth media is pumped. The growth media, after passing over the cells, is then contacted with an NO sensor that measures the concentration of NO in the growth media.

As used herein, "growth media" is simply any media that supports the growth of cells, be it of a commercially available variety, or one that is specially formulated for this purpose.

The present invention is further directed to an apparatus and a method for measuring the rate of consumption of $O_2$ by living cells. The apparatus allows the concentration of $O_2$ in a cell culture to be measured continuously, directly, quantitatively, and without destruction of the cells. According to the method for measuring $O_2$ consumption, the living cells are adhered to the inner wall of a tube through which growth media is pumped. The concentration of $O_2$ in the growth media that has not contacted the living cells is measured, the concentration of $O_2$ in the growth media that has contacted the living cells is measured, and the two concentration values are compared.

The present invention works on living cells. These cells may be obtained from a living organism and then subject to various processing techniques for isolation and purification purposes. The cells may also be grown in culture dishes. This may be done under controlled temperature and environmental conditions, such as inside a humidified incubator at a temperature of about 37° C. and in an air/5% $CO_2$ gas environment.

A growth media, such as DMEM with 5-10% bovine serum albumin and 1% antibiotic may be used to nourish the cells. The cells are grown until they reach confluence in the culture dishes, i.e., until there is a single, even layer of cells covering the bottom of the culture dish. Typically, this takes about 24-48 hours. The cells are then re-suspended in the growth media by gentle scraping, and then mixing and agitating the cells by repeatedly drawing the cells into a small syringe. This allows the cells to, at least temporarily, stay fairly well mixed in the growth media, and also partially activates the cells so they are prepared to adhere.

The cells within the small syringe are eventually introduced into a tube 126 seen in the apparatus 100 of in FIG. 1. This can be done in a number of ways. For example, a roller pump may be used to introduce the suspended cells within the syringe into a removable tube 126 that later is placed in the apparatus 100. Preferably, the roller pump introduces the suspended cells into the tube 126 at a flow rate of about 0.06 to about 0.1 mL/min. In a specific example, a flow rate of about 0.049 ml/min. was used for about 2-3 minutes to draw the cells into the tube, which was held at an angle of between 30-45° relative to the horizontal. The flow was then stopped and the tube 126 was positioned horizontally and kept in an incubator for about 15 minutes. During this 15 minute period of stopped flow, the cells adhered to the inside of the tubing. After 15 minutes, the tube 126 was inserted into the apparatus of the invention. Care was taken to not allow trapped gas bubbles to pass through the column when the flow of growth media is resumed.

Once the cells are adhered on the inner surface of the tube 126, the roller pump 104 pumps growth media through the tube 126 to nourish the cells. FIG. 1a is an exploded view of the tube 126 showing the living cells 133 adhered to the inner surface of the tube and molecules of gas 134 (e.g., $O_2$, $CO_2$, or NO) flowing through the tube.

The apparatus 100 includes a vessel 102A containing a first type of growth media that will support growth of the cells. Preferably, the vessel is maintained at a constant temperature, such as about 37° C., using a temperature control device 132. Temperature control device 132 may be a thermostated bath, electric heater, or the like.

The inlet of a tube 106 is inserted in the growth media. A roller pump 104 then pumps the growth media through the tube 106. control of roller pump 104 helps regulate convective mixing downstream by adjusting the flow rate of growth media. Any roller pump known to those skilled in the art can be used in the apparatus of the invention. A suitable roller pump for use in the apparatus of the invention is an Ismatec Pump (commercially available from Cole-Palmer of Chicago, Ill.).

Tube 106 is connected to the input 144 of a first gas equilibrator 108. The output 146 of gas equilibrator 108 is connected to input 110A of a switching valve 110. Switching valve 110 has, in addition to inlet 110A, inlet 110C and two outlets 10B and 110D. Outlet 110B is connected to the inlet of a tube 126 containing living cells adhered on the inner surface thereof. The outlet end of the tube 126 is connected to input 112D of a second switching valve 112. The second switching valve 112 has, in addition to inlet 112D, inlet 112B and outlets 112C and 112A. Outlet 112A is connected to a NO probe 114 for measuring NO concentrations and outlet 112C is connected to an $O_2$ probe 116 for measuring $O_2$ concentrations. Outlet probe 112C, however, may be connected to any other probe such as a probe for measuring $CO_2$ concentrations or pH. Typically, the NO probe and the $O_2$ probe are connected to a computer 128. Inlet 110C of switching valve 110 is connected to the outlet of a NO equilibrator 120 via T-connector 124. The inlet end of the NO equilibrator 120 is connected to the outlet end of a deoxygenator 122. The inlet end of the deoxygenator 122 is connected to a pump 130 that supplies water to the deoxygenator.

The pump 130 may be controlled by a computer 135 that regulates the flow from the pump 130. A suitable pump 130 for use in the apparatus and methods of the invention is a syringe pump, Model 11 VPF commercially available from Harvard Apparatus of Holliston, Mass.

As seen in FIG. 1, a second tube 106' may be used to supply a second type of growth media from a second vessel 102B. While FIG. 1 shows two discrete vessels 102A and 102B, it is understood that tubes 106, 106' may feed identical growth media from a common vessel. As seen in FIG. 1, the roller pump 104 pumps the growth media from second vessel 102B through the tube 106'. Tube 106' is connected to the input of a second gas equilibrator 108'.

The outlet of the second gas equilibrator 108' is connected to a first inlet 124A of T-connector 124 while the outlet of NO equilibrator 120 is connected to a second inlet 124C of the T-connector 124. Thus, the T-connector merges the effluents from the second gas equilibrator and the NO equilibrator to create a blended effluent that emerges from an outlet 124B of the T-connector 124. As seen in FIG. 1, the outlet 124B of the T-connector is connected to input 110C of valve 110, thereby supplying the blended effluent to valve 110.

Preferably tube 126 is a cylindrical tube, however, topologically equivalent structures can be used. Preferably tube 126 is a capillary tube. Any capillary tube can be used. The capillary tube can be, for example, a silica glass tubing having an inside diameter of from about 0.01 mm to about 1 mm and an outside diameter of about 0.3 mm to about 1.5 mm and a length of from about 2 cm to about 100 cm. The inner surface of the capillary tube can be coated with a variety of internal coatings including, polar and non-polar coatings. For example, the inner surface of the capillary tube can be coated with a siloxane such as phenylmethylsiloxane or dimethylsiloxane. Typically, the coating can have a thickness of from about 2 microns to about 50 microns. A variety of capillary columns are commercially, for example, from Alltech Associates, Inc., Applied Science Lab, of Deerfield, Ill. or J.W. Scientific of Mission Viejo, Calif. A suitable capillary tube for use in the apparatus and methods of the invention is a fused silica gas chromatography tube, 0.8 mm OD, and 0.53 mm ID, about 10 cm long, coated with dimethylsiloxane at a thickness of 10 microns (commercially available from Alltech Associates, Inc., Applied Science Lab, Deerfield, Ill.).

Figure 2:
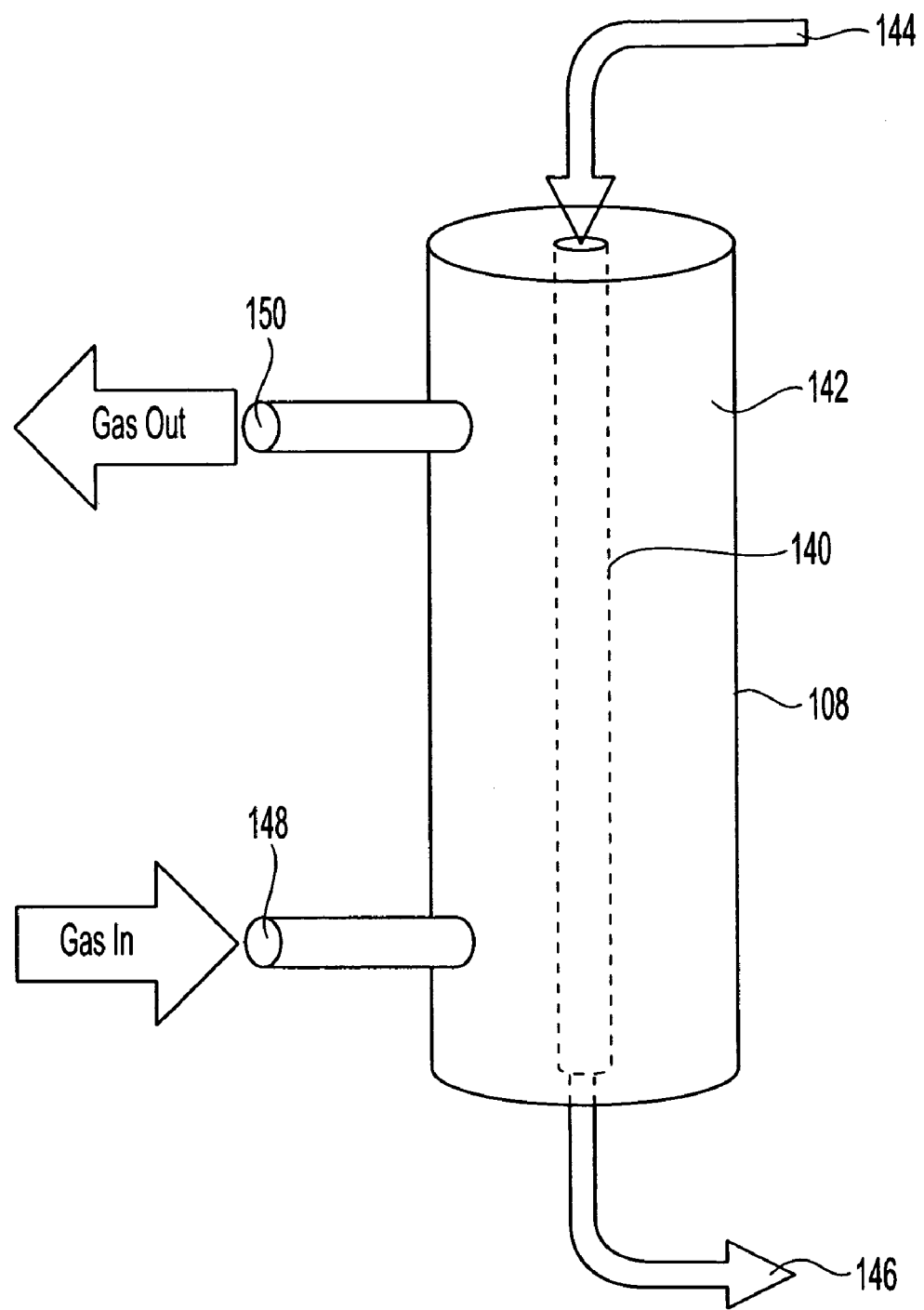
FIG. 2 is a schematic of the equilibrator used in the method of the invention.

The gas equilibrators 108 and 108' equilibrate the growth media with $O_2$ and $CO_2$. A schematic of the gas equilibrators is shown FIG. 2. The gas equilibrators comprise a piece of silicone tubing 140 (commercially available from Dow Chemical Company of Midland, Mich.) through which the growth media flows from input end 144 to output end 146. The flow of growth media through the silicone tubing is from about 0.2 mL/min to about 0.8 mL/min, preferably about 0.3 mL/min to about 0.7 mL/min, and most preferably about 0.5 to about 0.6 mL/min. The silicone tubing is then surrounded by a piece of Tygon® tubing (commercially available from Cole-Palmer of Chicago, Ill.) 124 through which the gases $O_2$ and $CO_2$ flow at partial pressures of $PO_2$ and $PCO_2$, respectively, from input end 148 to output end 150. The $O_2$ and $CO_2$ diffuse through the silicone tubing into the growth media such that the concentration of $O_2$ and $CO_2$ in the growth media is proportional to the partial pressures of $O_2$ and $CO_2$ in the Tygon® tubing. The equilibrators allow the partial pressures of $O_2$ and $CO_2$ to be precisely controlled, thereby causing the concentrations of $O_2$ and $CO_2$ in the growth media to be precisely controlled, as well.

The silicone tubing has an inside diameter of from about 0.012 inches to about 0.065 inches, an outside diameter of about 0.020 inches to about 0.080 inches, and a length of from about 3 inches to about 10 feet. In one embodiment, the silicone tubing is about 3 feet long, and has an inside diameter of about 0.02 inches, and an outside diameter of about 0.32 inches.

The Tygon® tubing has an inside diameter that is larger than the outside diameter of the silicone tubing. The inside diameter of the Tygon® tubing is about 10 to 70 percent larger than the outside diameter of the silicone tubing, preferably about 15 to 60 percent larger than the outside diameter of the silicone tubing, and more preferably about 20 to 50 percent larger than the outside diameter of the silicone tubing. The length of the Tygon® tubing is typically about the same length as the length of the silicone tubing. Suitable Tygon® tubing for use in the apparatus and methods of the invention is Cole-Palmer Masterflex #16 pump tubing that has an ID of 0.12 inches and an OD of 0.25 inches (commercially available from Cole-Palmer of Chicago, Ill.).

The partial pressures of $O_2$ and $CO_2$ can range from about 0.1 torr to about 500 torr, preferably about 1 torr to about 300 torr, most preferably from about 5 torr to about 200 torr. In one embodiment the partial pressure of $O_2$ is about 100 torr and the partial pressure of the $CO_2$ is about 40 torr.

The deoxygenator 122 is used to deoxygenate water supplied by pump 130. Water is pumped through the silicone tubing using pump 130 and high purity nitrogen gas is pumped through the Tygon® tubing. The nitrogen gas diffuses through the silicone tubing into the water and displaces any oxygen in the water. Typically the nitrogen is at atmospheric pressure, although other pressures can also be used. Preferably, the nitrogen gas has less than 10 ppm of oxygen, more preferably less than about 5 ppm of oxygen, and most preferably less than about 1 ppm of oxygen. The deoxygenator 122 is similar in construction to the gas equilibrators in that the same silicone tubing is surrounded by the same Tygon® tubing as is used for the equilibrators 108 and 108'. Typically, however, the deoxygenator 122 is only from about 3 inches to about 5 feet in length.

The NO equilibrator 120 is used to introduce a predetermined amount of nitrogen gas containing NO into the deoxygenated water. Typically, the nitrogen gas contains from about 100 ppm to about 10,000 ppm of NO, preferably about 500 ppm to 7,500 ppm of NO, and more preferably about 1,000 ppm to about 5,000 ppm of NO. In one embodiment the nitrogen gas contains about 2,000 ppm of NO. The nitrogen gas diffuses through the silicone tubing and into the water to provide a concentration of NO in the water that is proportional to the partial pressure of NO in the nitrogen gas in the Tygon® tubing. Typically the nitrogen gas containing NO is at atmospheric pressure, although other pressures can be used. The NO equilibrator 120 is also similar in construction to equilibrators 108 and 108'. The same silicone tubing and Tygon® tubing is used for the NO equilibrator as is used for the equilibrators 108 and 108'. The NO equilibrator, however, is typically only from about 2 inches to about 1 feet in length, preferably about 6 inches in length. Since the NO equilibrator is mixed with the water after the water has been deoxygenated, oxidation of the NO is minimized. Highly purified nitrogen, as described above, is used.

Preferably, the water that is pumped through the deoxygenator and the NO equilibrator is distilled water. It has been observed that adding NO to water that is later mixed with the growth media is preferable to adding NO directly to the growth media in equilibrators 108 and/or 108'. This may be because oxidation of the NO is catalyzed by anions that are present in the growth media. Thus, it is preferable to minimize contact of the NO with the anions in the growth media to the extent possible.

Any switching valve known to those skilled in the art can be used in the apparatus and methods of the method. A suitable valve for use in the apparatus and methods of the invention is a 2-position 4-port switching valve model no. EH2N4WE commercially available from Valco Inc. of Sarasota, Fla.

Any NO sensor known to those skilled in the art can be used in the apparatus and methods of the method. A suitable NO sensor for use in the apparatus and methods of the invention is a model ISO-NO Mark II commercially available from World Precision Instruments of Sarasota, Fla.

Any $O_2$ sensor known to those skilled in the art can be used in the apparatus and methods of the method. A suitable $O_2$ sensor for use in the apparatus and methods of the invention is a model no. IS0-11 commercially available from World Precision Instruments of Sarasota, Fla.

The apparatus of the present invention allows the amount of NO produced by the cells growing on an inner surface of the tube 126 to be measured without destroying the cells. In addition, the NO measurements may be made continuously so long as a fluid flows through the tube 126. Production of NO by cells in the tube 126 can be measured by positioning valve 110 so that inlet 110A and outlet 110B are connected and positioning valve 112 so that inlet 112D and outlet 112A are connected. In this configuration, growth media equilibrated with $O_2$ and $CO_2$ is directed to flow through tube 126 containing the living cells. The outlet of tube 126 then flows through valve 112 to the NO probe wherein the concentration of the NO in the growth media is easily and directly measured by the NO probe and then recorded on the computer. Importantly, the apparatus of the invention allows the concentration of NO to be determined directly and does not require determining the concentration of oxidation products of NO (i.e., $NO_2$ and $NO_3$). Without wishing to be bound by theory it is believed that in the apparatus of the invention there is very short transit times between the production of NO by the cells and the when the growth media containing the NO reaches the NO sensor. Thus, there is insufficient time for the NO produced by the cells to be oxidized to $NO_2$ and/or $NO_3$.

Importantly, the apparatus of the invention also allows the NO probe to be easily calibrated. By (a) controlling valve 110 so that inlet 110C and outlet 110D are connected and (b) controlling valve 112 so that inlet 112B and outlet 112A are connected and (c) controlling T-connector 124 so that the effluent from the NO equilibrator and second gas equilibrator 108' are combined, the output from the NO equilibrator 120 and equilibrator 108' by-passes the cell-containing tube 126 and flows directly to the NO sensor 114. The concentration of NO in the growth media is then measured by the NO sensor 114. Since the concentration of NO in the effluent from the NO equilibrator is known and the ratio of the amount of effluent from the NO equilibrator to the amount of effluent from equilibrator 108' is known, the concentration of NO in the growth media can be easily determined. This value for NO concentration is then used to calibrate the NO sensor 114. The ratio of effluent from the NO equilibrator 120 to effluent from equilibrator 108', the mixing ratio, is typically about 1:100, although other ratios can be used. For example, if the concentration of NO in the effluent from the NO equilibrator 120 is 2,000 ppm, a mixing ratio of about 1:100 results in an NO concentration of about 20 ppm. Also by (a) controlling valve 110 so that inlet 110A and outlet 110D are connected and (b) controlling valve 112 so that inlet 112B and outlet 112A are connected, tube 126 is bypassed and growth media from first gas equilibrator 108 is directed to the NO sensor. This configuration allows a "baseline level" for NO in the growth media to be measured.

The apparatus of the invention also allows the concentration of $O_2$ in the growth media to be readily determined. By (a) controlling valve 110 so that inlet 110A and outlet 110D are connected (as seen in FIG. 1), and (b) controlling valve 112 so that inlet 112B and outlet 112C are connected (as seen in FIG. 1), the growth media, equilibrated with $O_2$ and $CO_2$, is directed to a bypass 129 around the tube 126 and so flows directly to the $O_2$ probe wherein the concentration of $O_2$ in the growth media can be recorded directly.

The apparatus 100 also can used to measure cellular respiration. This is done by measuring and then comparing the partial pressures of $O_2$ in growth media that has and that has not passed over the cells in tube 126. By (a) controlling valve 110 so that inlet 110A and outlet 110B are connected and (b) controlling valve 112 so that inlet 112D and outlet 112C are connected, the growth media from the first gas equilibrator 108, after passing over the cells in tube 126, flows directly to the $O_2$ probe. This gives the concentration of $O_2$ in the growth media that has been passed over (and thus has been exposed to) the cells. Now, by (a) controlling valve 110 so that inlet 110A and outlet 110D are connected and (b) controlling valve 112 so that inlet 112B and outlet 112C are connected, the concentration of $O_2$ in the growth media from first gas equilibrator 108 that has not passed over (and thus has not been exposed to) the cells, can be measured. Cellular respiration is calculated from the difference between the concentration of $O_2$ in growth media not exposed to the cells and the concentration of $O_2$ in growth media exposed to the cells.

Cellular respiration is typically reported as the $VO_2$ value, the amount of $O_2$ that cells consume in mL/min; the $VCO_2$ value, the amount of $CO_2$ that cells consume in mL/min; or R, the ratio $VCO_2/NO_2$. $VO_2$ (or $VCO_2$) is the amount of $O_2$ (or $CO_2$) entering the tube 126 less the amount of $O_2$ (or $CO_2$) leaving the tube. The amount of $O_2$ (or $CO_2$) entering the tube 126 equals the partial pressure of $O_2$ ($CO_2$) delivered to the tube 126 times the solubility of $O_2$ ($CO_2$) in the growth media flow rate, and the amount of $O_2$ (or $CO_2$) leaving the tube 126 equals the partial pressure of $O_2$ ($CO_2$) leaving the tube 126 times the solubility of $O_2$ ($CO_2$) in the growth media flow rate.

Each of these values is preset or readily determined with the apparatus of the invention. Thus, the apparatus of the invention allows oxygen consumption by the cells to be readily measured. Although the amount of oxygen in the growth media that is delivered to the cells is larger than uptake of oxygen by the cells, it is not so large that changes in concentration of the $O_2$ cannot be accurately measured. It is further noted that the $O_2$ probe can easily be replaced with another type of probe to measure the concentration of other gases, such as, for example, $CO_2$; a probe for measuring some other value, such as pH; or a combination probe that measures more than one parameter.

The apparatus 100 may be used to rapidly switch between growth media which differ in the partial pressures of a gas. This allows the concentration of $O_2$ (or other gas) in the growth media to which the cells are exposed, to be rapidly changed, thereby providing information on the effect on NO production by the cells in tube 126, when the partial pressure of $O_2$ (or other gas) is changed rapidly. Such a feature may be used as a model for the inflammatory response of cells that are exposed to intermittent hypoxia.

For example, gas equilibrator 108 can have a first partial pressure of oxygen, $P_A$, and gas equilibrator 108' can have a second partial pressure of oxygen, $P_B$. When valve 110 is controlled so that inlet 110A and outlet 10B are connected, the cells in tube 126 are exposed to growth media (from the first gas equilibrator 108) having a concentration of $O_2$ that is proportional to the partial pressure of oxygen $P_A$. If valve 110 is then rapidly switched so that inlet 110C and outlet 110B are connected while pump 130 is turned off (and/or T-valve 124 is controlled to prevent the introduction of NO-laden water) the cells in tube 126 will then be exposed to growth media (from second gas equilibrator 108') having a concentration of $O_2$ that is proportional to the partial pressure of oxygen $P_B$. If, during this process, valve 112 is controlled so that inlet 112D and outlet 112A are connected, the change in concentration of NO caused by the change in partial pressure of $O_2$ from $P_A$ to $P_B$ can be measured. Preferably, the valve 110 allows the concentration of $O_2$ to be changed in less than about 500 msec, preferably less than about 400 msec, and most preferably less than about 200 msec.

The apparatus of the present invention thus allows the cells in tube 126 to first be exposed to growth media equilibrated with gas at a first known partial pressure of oxygen (from first gas equilibrator 108) and then be exposed to growth media equilibrated with gas at a second known partial pressure of oxygen (from second gas equilibrator 108'), in rapid succession. One skilled in the art should readily recognize the present invention also allows for this order to be reversed. Using two equilibrated streams of growth media and a switching valve 110 to switch between the streams makes it possible to rapidly change the concentration of oxygen that cells are exposed to at the cellular level in a controlled manner.

The apparatus 100 may also be used to rapidly switch between growth media which differ in a property other than in the partial pressures of a gas. One use of this is to study the effect of soluble stimuli on the production of NO and/or the consumption of $O_2$. Examples of such stimuli include, but are not limited to, LPS and interferon. For example, equilibrators 108 and 108' could each have the same partial pressure of $O_2$ and $CO_2$ but the growth media flowing through equilibrator 108 comes from vessel 102A free of stimuli, while the growth media flowing through equilibrator 108' comes from vessel 102B which has stimuli therin. By rapidly changing from stimulus-free growth media to stimulas-laden growth media (or vice-versa), one may study the effects on the same cells under these two different conditions.

One contemplated use is to measure for the presence of NO as a messenger in an immune response, and assessing the way cells change their immune activation in response to specific stimuli. Cells from a patient could be placed in the tube 126 to assess that patient's immune response and elicit diagnostic information. Relevant cell types that can easily be collected from patients include: alveolar macrophages from broncho-alveolar lavage (BAL) fluid in pulmonary disease, especially acute respiratory distress syndrome (ARDS); monocytes in blood samples; peritoneal macrophages from peritoneal lavage; and cells from tissue biopsies.

Table 1 summarizes the effluent that is sent to the NO detector and the effluent that is sent to the $O_2$ detector for various configurations of the 2-position 4-port valves 110 and 112 with the pump 130 in the on and off positions. In Table 1, position #1 for valve 110 is when input port 110A is connected to output port 110D and input port 110C is connected to output port 110B (as shown in FIG. 1) while position #2 for valve 110 is when input port 110A is connected to output port 10B and input port 110C is connected to output port 10D (alternative to what is shown in FIG. 1). Similarly, position #1 for valve 112 is when input port 112D is connected to output port 112A and input port 112B is connected to output port 112C (as shown in FIG. 1) while position #2 for valve 112 is when input port 112D is connected to output port 112C and input port 112B is connected to output port 112A (alternative to what is shown in FIG. 1).

TABLE I

Effect of Various Positions of the 2-Position 4-Port Valves in the Apparatus of FIG. 1.

| Position of Valve 110 | Position of Valve 112 | Status of Pump 130 | NO sensor contacts | Oxygen sensor contacts | Significance/Use |
|---|---|---|---|---|---|
| #2 | #2 | on | effluent from $2^{nd}$ gas equilibrator 108' + effluent from NO equilibrator 120 bypassing the cells | effluent from $1^{st}$ gas equilibrator 108 exposed to cells | a) standardize NO sensor using known conc. in NO equilibrator 120 b) measure $O_2$ consumption by cells exposed only to effluent from $1^{st}$ gas equilibrator; |
| #2 | #1 | on | effluent from $1^{st}$ gas equilibrator 108 exposed to cells | effluent from $2^{nd}$ gas equilibrator 108' + effluent from NO equilibrator 120 bypassing the cells | a) measure NO production by cells exposed only to effluent from $1^{st}$ gas equilibrator 108 b) standardize $O_2$ sensor using known concentration of $O_2$ in effluent from $2^{nd}$ gas equilibrator 108' |
| #1 | #2 | on | effluent from $1^{st}$ gas equilibrator 108 bypassing the cells | effluent from $2^{nd}$ gas equilibrator 108' + effluent from NO equilibrator 120 exposed to cells | a) set zero point of NO sensor using effluent from $1^{st}$ gas equilibrator 108 b) measure $O_2$ consumption by cells using effluent of $2^{nd}$ gas equilibrator 108' in the presence of external NO |

TABLE I-continued

Effect of Various Positions of the 2-Position 4-Port Valves in the Apparatus of FIG. 1.

| Position of Valve 110 | Position of Valve 112 | Status of Pump 130 | NO sensor contacts | Oxygen sensor contacts | Significance/Use |
|---|---|---|---|---|---|
| #1 | #1 | on | effluent from $2^{nd}$ gas equilibrator 108' + effluent from NO equilibrator 120 exposed to cells | effluent from $1^{st}$ gas equilibrator 108 bypassing the cells | a) measure (additional) NO production by cells exposed to effluent from $2^{nd}$ gas equilibrator 108' in the presence of external NO b) standardize $O_2$ sensor using known concentration of $O_2$ in effluent from $1^{st}$ gas equilibrator 108 |
| #2 | #2 | off (no NO) | effluent from $2^{nd}$ gas equilibrator 108' bypassing the cells | effluent from $1^{st}$ gas equilibrator 108 exposed to cells | a) set zero point of NO sensor using effluent from $2^{nd}$ gas equilibrator 108' b) measure $O_2$ consumption by cells exposed only to effluent from $1^{st}$ gas equilibrator 108 |
| #2 | #1 | off (no NO) | effluent from $1^{st}$ gas equilibrator 108 exposed to cells | effluent from $2^{nd}$ gas equilibrator 108' bypassing the cells | a) measure NO production by cells exposed only to effluent from $1^{st}$ gas equilibrator 108 b) standardize $O_2$ sensor using known concentration of $O_2$ in effluent from $2^{nd}$ gas equilibrator 108' |
| #1 | #2 | off (no NO) | effluent from $1^{st}$ gas equilibrator 108 bypassing the cells | effluent from $2^{nd}$ gas equilibrator 108' exposed to cells | a) set zero point of NO sensor using effluent from $1^{st}$ gas equilibrator 108 b) measure $O_2$ consumption by cells exposed only to effluent from $2^{nd}$ gas equilibrator 108' |
| #1 | #1 | off (no NO) | effluent from $2^{nd}$ gas equilibrator 108' exposed to cells | effluent from $1^{st}$ gas equilibrator 108 bypassing the cells | a) measure NO production by cells exposed only to effluent from $2^{nd}$ gas equilibrator 108' b) standardize $O_2$ sensor using known concentration of $O_2$ in effluent from $1^{st}$ gas equilibrator 108 |

Once measurements have been made using the apparatus of the invention, the cell number or total amount of cells present in the tube 126 can be determined so that the measured value of, for example, NO production or $O_2$ consumption, can be quantified. The cell number or total amount of cells present in tube 126 can be determined by lysing the cells by freezing and then thawing the tube 126, collecting the fluid with the lysed cell contents from the tube 126, and then measuring the protein concentration with a standard commercial kit, such as the Bio-Rad protein assay (commercially available from Bio-Rad of Hercules, Calif.). It has been shown that there is a generally linear correlation between protein concentration and cell number for cultured macrophages (C. M. Otto and J. E. Baumgardner, *Am. J. Physiol. Cell Physiol.* 280:C280-C287, (2001)).

The present invention is not to be limited in scope by the specific embodiments disclosed herein which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited, the entire disclosures of which are incorporated herein by reference.

What is claimed is:

1. A nitric oxide (NO) measuring apparatus comprising:

a first gas equilibrator having an inlet and an outlet, the first gas equilibrator configured to maintain a first concentration of a first gas within a first fluid, when the first fluid flows through the first gas equilibrator and exits the first gas equilibrator as a first effluent;

a second gas equilibrator having an inlet and an outlet, the second gas equilibrator configured to maintain a second concentration of a second gas within a second fluid, when the second fluid flows through the second gas equilibrator and exits the second gas equilibrator as a second effluent;

a tubular member configured to accommodate passage of a fluid therethrough, the tubular member having an inner surface suitable for having living cells adhered thereto, said tubular member having an inlet and an outlet, wherein the inlet of the tubular member is in fluid communication with the outlet of the first gas equilibrator, when the apparatus is in a first configuration;

a first NO sensor in fluid communication with the first gas equilibrator via the tubular member, the first NO sensor configured to measure an NO concentration of the first effluent from the first gas equilibrator after the first effluent has flowed through the tubular member, when the apparatus is in said first configuration;

a first oxygen ($O_2$) sensor in fluid communication with the second gas equilibrator, the first oxygen sensor configured to measure an $O_2$ concentration of the second effluent from the second gas equilibrator without the second effluent having flowed through the tubular member, when the apparatus is in said first configuration; and one or more valves directing the first effluent to the inlet of the tubular member and thus to the first NO sensor, and directing the second effluent to the first $O_2$ sensor, when the apparatus is in said first configuration.

2. The apparatus according to claim 1, further comprising a first pump configured to supply said first fluid to said first gas equilibrator and a second pump configured to supply said second fluid to said second gas equilibrator.

3. The apparatus according to claim 2, wherein the first pump and the second pump are configured as a single unit.

4. The apparatus according to claim 1, wherein the second gas equilibrator is configured to maintain a concentration of NO within the second fluid.

5. The apparatus according to claim 4, wherein the second fluid is deoxygenated water and the apparatus further comprises a deoxygenator configured to supply said deoxygenated water to the second gas equilibrator.

6. The nitric oxide (NO) measuring apparatus according to claim 1, wherein said one or more valves are adjustable such that the apparatus may selectively occupy any of a plurality of configurations including:

said first configuration in which the first effluent passes through the tubular member and the NO sensor measures an NO concentration of said first effluent, while the second effluent bypasses the tubular member and an $O_2$ sensor measures an $O_2$ concentration of the second effluent;

a second configuration in which the first effluent passes through the tubular member and the $O_2$ sensor measures an $O_2$ concentration of said first effluent, while the second effluent bypasses the tubular member and an NO sensor measures an NO concentration of the second effluent;

a third configuration in which the second effluent passes through the tubular member and the NO sensor measures an NO concentration of said second effluent, while the first effluent bypasses the tubular member and an $O_2$ sensor measures an $O_2$ concentration of the first effluent;

a fourth configuration in which the second effluent passes through the tubular member and the $O_2$ sensor measures an $O_2$ concentration of said second effluent, while the first effluent bypasses the tubular member and an NO sensor measures an NO concentration of the first effluent.

7. A nitric oxide (NO) measuring apparatus comprising:

a first gas equilibrator having an inlet and an outlet, the first gas equilibrator configured to maintain a first concentration of a first gas within a first fluid, when the first fluid flows through the first gas equilibrator and exits the first gas equilibrator as a first effluent;

a second gas equilibrator having an inlet and an outlet, the second gas equilibrator configured to maintain a second concentration of a second gas within a second fluid, when the second fluid flows through the second gas equilibrator and exits the second gas equilibrator as a second effluent;

a tubular member configured to accommodate passage of a fluid therethrough, the tubular member having an inner surface suitable for having living cells adhered thereto, said tubular member having an inlet and an outlet, wherein the inlet of the tubular member is in fluid communication with the outlet of the first gas equilibrator, when the apparatus is in a first configuration;

a first NO sensor in fluid communication with the first gas equilibrator via the tubular member, the first NO sensor configured to measure an NO concentration of the first effluent from the first gas equilibrator after the first effluent has flowed through the tubular member, when the apparatus is in said first configuration;

a first oxygen ($O_2$) sensor in fluid communication with the second gas equilibrator, the first oxygen sensor configured to measure an $O_2$ concentration of the second effluent from the second gas equilibrator without the second effluent having flowed through the tubular member, when the apparatus is in said first configuration; and a first valve in fluid communication with the first and second gas equilibrators, the first valve configured to:

receive the first effluent from the first gas equilibrator;

receive the second effluent from the second gas equilibrator; and supply one of the first and second effluents to the inlet of the tubular member while directing the other of the first and second effluents to a bypass around the tubular member.

8. The apparatus according to claim 7, further comprising a second valve configured to:

receive a third effluent from the tubular member;

receive a fourth effluent from the bypass; and supply one of the third and fourth effluents to the first NO sensor while supplying the other of the third and fourth effluents to the first $O_2$ sensor.

9. A nitric oxide (NO) measuring apparatus comprising:

a first gas equilibrator having an inlet and an outlet, the first gas equilibrator configured to maintain a first concentration of a first gas within a first fluid, when the first fluid flows through the first gas equilibrator and exits the first gas equilibrator as a first effluent;

a second gas equilibrator having an inlet and an outlet, the second gas equilibrator configured to maintain a second concentration of a second gas within a second fluid, when the second fluid flows through the second gas equilibrator and exits the second gas equilibrator as a second effluent;

a third gas equilibrator having an inlet and an outlet, the third gas equilibrator configured to maintain a third concentration of a third gas within a third fluid, when said third fluid flows through the third gas equilibrator, wherein an effluent of the third gas equilibrator merges with the second effluent to thereby form a blended effluent;

a tubular member configured to accommodate passage of a fluid therethrough, the tubular member having an inner surface suitable for having living cells adhered thereto, said tubular member having an inlet and an outlet, wherein the inlet of the tubular member is in fluid communication with the outlet of the first gas equilibrator, when the apparatus is in a first configuration;

a first NO sensor in fluid communication with the first gas equilibrator via the tubular member, the first NO sensor configured to measure an NO concentration of the first effluent from the first gas equilibrator after the first effluent has flowed through the tubular member, when the apparatus is in said first configuration;

a first oxygen ($O_2$) sensor configured to measure an $O_2$ concentration of the blended effluent without the blended effluent having flowed through the tubular member, when the apparatus is in said first configuration; and one or more valves directing the first effluent to the inlet of the tubular member and thus to the first NO sensor, and directing the blended effluent to the first $O_2$ sensor, when the apparatus is in said first configuration.

10. The apparatus according to claim 9, further comprising a T-connection configured to merge effluents from the second gas equilibrator and the third gas equilibrator to thereby form the blended effluent, wherein the first oxygen ($O_2$) sensor is in fluid communication with the T-connection, when the apparatus is in said first configuration.

11. The apparatus according to claim 10, comprising a first valve configured to:
receive the first effluent from the first gas equilibrator;
receive the blended effluent from the T-connection; and
supply one of the first effluent and the blended effluent to the inlet of the tubular member while directing the other of the first effluent and the blended effluent to a bypass around the tubular member.

12. The apparatus according to claim 11, comprising a second valve configured to:
receive a third effluent from the tubular member;
receive a fourth effluent from the bypass; and
supply one of the third and fourth effluents to the first NO sensor while supplying the other of the third and fourth effluents to the first $O_2$ sensor.

13. The apparatus according to claim 12, wherein the third gas equilibrator is configured to maintain a concentration of NO within the third fluid.

14. The apparatus according to claim 13, wherein the third fluid is deoxygenated water and apparatus further comprises a deoxygenator configured to supply said deoxygenated water to the third gas equilibrator.

15. The nitric oxide (NO) measuring apparatus according to claim 9, wherein said one or more valves are adjustable such that the apparatus may selectively occupy any of a plurality of configurations including:

said first configuration in which the first effluent passes through the tubular member and the NO sensor measures an NO concentration of said first effluent, while the blended effluent bypasses the tubular member and the $O_2$ sensor measures an $O_2$ concentration of the blended effluent;

a second configuration in which the first effluent passes through the tubular member and the $O_2$ sensor measures an $O_2$ concentration of said first effluent, while the blended effluent bypasses the tubular member and an NO sensor measures an NO concentration of the blended effluent;

a third configuration in which the blended effluent passes through the tubular member and the NO sensor measures an NO concentration of said blended effluent, while the first effluent bypasses the tubular member and the $O_2$ sensor measures an $O_2$ concentration of the first effluent;

a fourth configuration in which the blended effluent passes through the tubular member and the $O_2$ sensor measures an $O_2$ concentration of said blended effluent, while the first effluent bypasses the tubular member and an NO sensor measures an NO concentration of the first effluent.

16. A gas measuring apparatus comprising:
a first gas equilibrator configured to maintain a first concentration of a gas within a first fluid;
a second gas equilibrator configured to maintain a second concentration of a gas within a second fluid;
a switching valve in fluid communication with the first gas equilibrator and the second gas equilibrator;
a tubular member having an inlet in fluid communication with an outlet of the switching valve, wherein the first gas and the second gas are separately and selectively fed through the switching valve to the tubular member;
a first gas sensor in fluid communication with an outlet of the tubular member, the first gas sensor being one of an NO or an $O_2$ sensor; and
a second gas sensor in fluid communication with the switching valve through a bypass around the tubular member, the second gas sensor being the other of an NO or an $O_2$ sensor.

17. The gas measuring apparatus of claim 16, wherein the switching valve is configured to alternate between feed of the first gas and the second gas to the tubular member in about 500 msec or less.

18. The gas measuring apparatus of claim 16, wherein the switching valve is configured to alternate between feed of the first gas and the second gas to the tubular member in about 400 msec or less.

19. The gas measuring apparatus of claim 16, wherein the switching valve is configured to alternate between feed of the first gas and the second gas to the tubular member in about 200 msec or less.

20. A nitric oxide (NO) measuring apparatus comprising:
a first gas equilibrator having an inlet and an outlet, the first gas equilibrator configured to maintain a first concentration of a first gas within a first fluid, when the first fluid flows through the first gas equilibrator and exits the first gas equilibrator as a first effluent;

a second gas equilibrator having an inlet and an outlet, the second gas equilibrator configured to maintain a second concentration of a second gas within a second fluid, when the second fluid flows through the second gas equilibrator and exits the second gas equilibrator as a second effluent;

a tubular member configured to accommodate passage of a fluid therethrough, the tubular member having an inner surface suitable for having living cells adhered thereto, said tubular member having an inlet and an outlet, wherein the inlet of the tubular member is selectively connectable to the outlet of one of the first and second gas equilibrators;

a first NO sensor selectively connectable to the outlet of the tubular member and configured to measure an NO concentration of one of the first and second effluents; and a first oxygen ($O_2$) sensor selectively connectable to the outlet of the tubular member and configured to measure an $O_2$ concentration of the other of the first and second effluents; wherein:

one or more valves selectively connect: the inlet of the tubular member to the outlet of one of the first and second gas equilibrators, the first NO sensor to the outlet of the tubular member and the first $O_2$ sensor to the outlet of the tubular member, such that the apparatus is capable of selectively occupying any of a plurality of configurations including:

a first configuration in which the first effluent passes through the tubular member and the NO sensor measures an NO concentration of said first effluent, while the second effluent bypasses the tubular member and the $O_2$ sensor measures an $O_2$ concentration of the second effluent;

a second configuration in which the first effluent passes through the tubular member and the $O_2$ sensor measures an $O_2$ concentration of said first effluent, while the second effluent bypasses the tubular member and an NO sensor measures an NO concentration of the second effluent;

a third configuration in which the second effluent passes through the tubular member and the NO sensor measures an NO concentration of said second effluent, while the first effluent bypasses the tubular member and the $O_2$ sensor measures an $O_2$ concentration of the first effluent; and a fourth configuration in which the second effluent passes through the tubular member and the $O_2$ sensor measures an $O_2$ concentration of said second effluent, while the first effluent bypasses the tubular member and an NO sensor measures an NO concentration of the first effluent.

21. The apparatus according to claim 20, comprising a first valve in fluid communication with the first and second gas equilibrators, the first valve configured to:

receive the first effluent from the first gas equilibrator;
receive the second effluent from the second gas equilibrator; and
supply one of the first and second effluents to the inlet of the tubular member while directing the other of the first and second effluents to a bypass around the tubular member.

22. The apparatus according to claim 21, comprising a second valve configured to:

receive a third effluent from the tubular member;
receive a fourth effluent from the bypass; and
supply one of the third and fourth effluents to the first NO sensor while supplying the other of the third and fourth effluents to the first $O_2$ sensor.

23. A nitric oxide (NO) measuring apparatus comprising:

a first gas equilibrator having an inlet and an outlet, the first gas equilibrator configured to maintain a first concentration of a first gas within a first fluid, when the first fluid flows through the first gas equilibrator and exits the first gas equilibrator as a first effluent;

a second gas equilibrator having an inlet and an outlet, the second gas equilibrator configured to maintain a second concentration of a second gas within a second fluid, when the second fluid flows through the second gas equilibrator and exits the second gas equilibrator as a second effluent;

a third gas equilibrator having an inlet and an outlet, the third gas equilibrator configured to maintain a third concentration of a third gas within a third fluid, when said third fluid flows through the third gas equilibrator, wherein an effluent of the third gas equilibrator merges with the second effluent to thereby form a blended effluent;

a tubular member configured to accommodate passage of a fluid therethrough, the tubular member having an inner surface suitable for having living cells adhered thereto, said tubular member having an inlet and an outlet, wherein the inlet of the tubular member is selectively connectable to receive either the first effluent or the blended effluent;

a first NO sensor selectively connectable to the outlet of the tubular member and configured to measure an NO concentration of one of the first and blended effluents; and a first oxygen ($O_2$) sensor selectively connectable to the outlet of the tubular member and configured to measure an $O_2$ concentration of the other of the first and blended effluents; wherein:

one or more valves selectively connect: the inlet of the tubular member to receive either the first effluent or the blended effluent, the first NO sensor to the outlet of the tubular member and the first $O_2$ sensor to the outlet of the tubular member such that the apparatus is capable of selectively occupying any of a plurality of configurations including:

a first configuration in which the first effluent passes through the tubular member and the NO sensor measures an NO concentration of said first effluent, while the blended effluent bypasses the tubular member and the $O_2$ sensor measures an $O_2$ concentration of the blended effluent;

a second configuration in which the first effluent passes through the tubular member and the $O_2$ sensor measures an $O_2$ concentration of said first effluent, while the blended effluent bypasses the tubular member and an NO sensor measures an NO concentration of the blended effluent;

a third configuration in which the blended effluent passes through the tubular member and the NO sensor measures an NO concentration of said blended effluent, while the first effluent bypasses the tubular member and the $O_2$ sensor measures an $O_2$ concentration of the first effluent; and a fourth configuration in which the blended effluent passes through the tubular member and the $O_2$ sensor measures an $O_2$ concentration of said blended effluent, while the first effluent bypasses the tubular member and an NO sensor measures an NO concentration of the first effluent.

24. The apparatus according to claim 23, further comprising a T-connection configured to merge effluents from the second gas equilibrator and the third gas equilibrator to thereby form the blended effluent.

25. The apparatus according to claim 24, comprising a first valve configured to:

receive the first effluent from the first gas equilibrator;
receive the blended effluent from the T-connection; and
supply one of the first and blended effluents to the inlet of the tubular member while directing the other of the first and blended effluents to a bypass around the tubular member.

26. The apparatus according to claim 25, comprising a second valve configured to:

receive a third effluent from the tubular member;
receive a fourth effluent from the bypass; and
supply one of the third and fourth effluents to the first NO sensor while supplying the other of the third and fourth effluents to the first $O_2$ sensor.

* * * * *